(12) United States Patent
Chetty et al.

(10) Patent No.: US 11,709,163 B2
(45) Date of Patent: Jul. 25, 2023

(54) METHODS FOR SIMULTANEOUS DETERMINATION OF SEROLOGICAL PROFILE AND ESTIMATION OF DURATION POST HIV INFECTION

(71) Applicant: AVIOQ, INC, Research Triangle Park, NC (US)

(72) Inventors: Chamroen Chetty, Durham, NC (US); Xing Xiang Li, Cary, NC (US)

(73) Assignee: AVIOQ, INC., Research Triangle Park, NC (US)

( * ) Notice: Subject to any disclaimer, the term of this patent is extended or adjusted under 35 U.S.C. 154(b) by 1751 days.

(21) Appl. No.: 15/509,841

(22) PCT Filed: Oct. 7, 2015

(86) PCT No.: PCT/US2015/054393
§ 371 (c)(1),
(2) Date: Mar. 8, 2017

(87) PCT Pub. No.: WO2016/057617
PCT Pub. Date: Apr. 14, 2016

(65) Prior Publication Data
US 2017/0307613 A1    Oct. 26, 2017

Related U.S. Application Data

(60) Provisional application No. 62/061,569, filed on Oct. 8, 2014.

(51) Int. Cl.
| | | |
|---|---|---|
| A61K 39/00 | (2006.01) | |
| C07K 16/10 | (2006.01) | |
| C07K 14/005 | (2006.01) | |
| A61K 39/21 | (2006.01) | |
| C07K 14/16 | (2006.01) | |
| G01N 33/569 | (2006.01) | |
| G01N 33/00 | (2006.01) | |

(52) U.S. Cl.
CPC ....... *G01N 33/56988* (2013.01); *G01N 33/00* (2013.01); *G01N 2333/16* (2013.01)

(58) Field of Classification Search
CPC ... A61P 31/18; C07K 2317/76; C07K 14/005; C07K 16/1063; A61K 2039/505
See application file for complete search history.

(56) References Cited

U.S. PATENT DOCUMENTS

| | | | |
|---|---|---|---|
| 2007/0026386 A1* | 2/2007 | Wilson | G01N 33/56988 |
| | | | 435/5 |
| 2009/0258343 A1 | 10/2009 | Reiter | |
| 2011/0003280 A1 | 1/2011 | Takahama et al. | |
| 2011/0045017 A1 | 2/2011 | Lian et al. | |
| 2012/0179421 A1 | 7/2012 | Dasgupta | |
| 2013/0157889 A1* | 6/2013 | Chilkoti | A61B 5/150358 |
| | | | 506/18 |

FOREIGN PATENT DOCUMENTS

| | | |
|---|---|---|
| AU | 2003283116 | 6/2004 |
| CN | 1251614 | 4/2000 |
| CN | 102680681 A | 9/2012 |
| CN | 104237510 | 12/2014 |
| EP | 0386713 A2 | 9/1990 |
| EP | 0461462 A1 | 12/1991 |
| EP | 0709680 * | 5/1996 |
| EP | 0709680 A1 | 5/1996 |
| RU | 2283497 C1 | 9/2006 |
| WO | 9321346 A1 | 10/1993 |
| WO | 9523973 A2 | 9/1995 |
| WO | WO1995023973 * | 9/1995 |
| WO | 2004048615 A1 | 6/2004 |
| WO | 2012127473 A1 | 9/2012 |
| WO | 2013178737 A1 | 12/2013 |
| WO | 2014071411 A1 | 5/2014 |
| WO | WO2014071411 * | 5/2014 |

OTHER PUBLICATIONS

Granade et al. Development of a Novel Rapid HIV Test for Simultaneous Detection of Recent or Long-Term HIC Type 1 Infection Using a Single Testing Device'; AIDS Research and Human Retroviruses; Jan. 2013, vol. 29, No. 1:61-67.*
Su, "Research Progress in Detection Technology of New HIV Infection", Chinese Journal Diagnostics, Electronic Edition (first issue), Nov. 30, 2013, p. 69-71, vol. 1, No. 1.

* cited by examiner

*Primary Examiner* — Barry A Chestnut
(74) *Attorney, Agent, or Firm* — FisherBroyles, LLP

(57) ABSTRACT

The present invention discloses a method and its variations for simultaneous detection of antibodies against two or more antigens of human immunodeficiency virus (HIV) and determination of approximate time (duration) post HIV infection, thereby confirming the infection, and determination of recency of an HIV infection. The number of individuals with recently infected HIV in a given period may be further used to estimate incidence of HIV in a population.

40 Claims, 3 Drawing Sheets

METHODS FOR SIMULTANEOUS DETERMINATION OF SEROLOGICAL PROFILE AND ESTIMATION OF DURATION POST HIV INFECTION

CROSS-REFERENCE TO RELATED APPLICATIONS

The present application is a 371 national phase entry of international application PCT/US2015/054393, filed Oct. 7, 2015, which claims priority to provisional patent application No. 62/061,569 filed Oct. 8, 2014, which are incorporated herein by reference in their entireties.

FIELD OF THE INVENTION

This invention relates to methods for simultaneous detection of antibodies against two or more antigens of human immunodeficiency virus (HIV) and determination of approximate time (duration) post HIV infection, thereby confirming the infection, and determination of recency of an HIV infection. The number of individuals with recently infected HIV in a given period may be further used to estimate incidence of HIV in a population.

BACKGROUND

Infection of human immunodeficiency virus (HIV) results in replication of the virus in T lymphocytes. Replication of HIV leads to an increase in the amounts of viral components, e.g., nucleic acids and proteins. Production of viral proteins elicits the host's immune responses, including the production of antibodies specific for HIV antigens. Diagnosis of an HIV infection can be accomplished through direct detection of a viral component, i.e., viral nucleic acids or proteins or indirect detection of the elicited antibodies against an HIV antigen. As nucleic acids can be amplified using a variety of methods, e.g., polymerase chain reaction (PCR), viral nucleic acid can be detected at the earliest time point after an infection, which is followed by viral proteins and, still later, by antibodies specific for the viral antigens.

Ascertained diagnosis of an HIV infection normally involves two steps: initial diagnosis using an HIV diagnostic test, followed by confirmation of initially reactive samples using a more specific confirmatory test. Initial diagnosis of an HIV infection via detection of HIV antigen specific antibodies is the most economical and widely used method for diagnosis of an HIV infection. These assays or tests are commonly known as diagnostic or screening assays or tests. The most commonly used assays for detection of HIV antibodies in a sample are those known as enzyme immunoassays (EIA), enzyme-linked immunosorbent assay (ELISA), and the lateral flow based immunoassays. Because these methods may produce false positive test results, samples that are tested as positive by these assays need to be further tested to confirm the infection using another type of assay, commonly known as HIV confirmatory or HIV supplemental tests.

One commonly used confirmatory test is the Western Blot assay, which is capable of detecting and differentiating antibodies against more than one HIV antigen. When a Western Blot test is used, an HIV infection is confirmed when the antibodies in the samples react with any two or more of the following HIV antigens: p24, p65, gp41 and/or gp120/gp160. However, performing a Western Blot test is time-consuming and labor-intensive, and the results are often very subjective.

In recent years, it has been recognized that without an effective vaccine or therapeutic cure, the most effective means to further reduce the spread of HIV today is prevention. Consequently, enormous effort and resources are being devoted to various HIV prevention programs. The effectiveness of a prevention program could be monitored by measuring the new infection rate, or incidence, in a population. Traditionally, HIV incidence was determined by following a study cohort representing a population, which is an expensive and difficult method. Consequently, HIV infection "regency" or recency tests were developed. These tests were designed to determine whether an infection occurs recently (e.g., within 12 months). The rate of recent infections in a population in a certain period of time, for example 6 months, 12 months, 18 months, or 24 months, is the HIV incidence of the population. HIV incidence is an important tool for epidemiologic characterization, assessing the effectiveness of HIV/AIDS prevention program, and in the design and evaluation of HIV intervention trials.

Three different types of serologic assays have been developed for HIV recency testing. These tests include the "detuned" assay that essentially assesses antibody titers at one time-point, the BED-CEIA assay that measures the percentage of IgG directed against an HIV antigen as compared with total IgG, and the avidity assays that measure the strength of antibody-antigen binding. Among these assays, the avidity assay appeared to be the most accurate assay for recency determination of an HIV infection. One of the avidity assays uses an undercoated solid phase for recency detection, which is called limiting antigen avidity EIA or LAg Avidity-EIA as published in scientific publications (Wei et al., *Aids Res Hum Retroviruses*. 2010; 26:61 and Duong et al., *PLoS One*. 2012; 7:e33328), which are cited here solely as references. The LAg Avidity-EIA is based on the observation that longer HIV infection results in more antibodies with higher affinity (i.e., strong binding) and/or better avidity for HIV antigens and thus more bound antibodies even on a solid phase with undercoated antigens.

However, these recency tests can only be performed on samples that have been previously confirmed positive for HIV antibodies, i.e., those samples that have been subjected to testing using a confirmatory test. Because of the disconnection between the initial HIV-1 diagnosis and the recency testing, not all HV-1 positive samples are tested for new infection, thereby leading to possible inaccurate estimation of the incidence in a population. Moreover, because at least two tests are performed for HIV infection recency detection of a sample, it is still costly to estimate the HIV recency in a population.

The present invention provides methods that incorporate an HIV infection recency test into a confirmatory test so that all HIV positive samples confirmed by the assay will automatically have recency test results. Widespread adoption of the assay will significantly increase the sample size for HIV incidence estimation, leading to more accurate estimation of HIV incidence in a population. Since all samples initially reactive with an HIV diagnostic test should go through confirmation testing anyway, the cost of obtaining significantly more recency test results for estimation of HIV incidence in a population will not be significantly more than performing confirmatory testing itself when HIV recency testing is incorporated into confirmatory testing.

According to the present invention, various additional functionalities can be added to the assay. The functionalities include, but are not limited to, differentiation between HIV-1 and HIV-2 infection and diagnosis of specimens with unknown status of HIV infections.

SUMMARY OF THE INVENTION

In one embodiment, a method for determination of HIV infection and estimation of HIV infection recency is provided, the method comprising the steps of: a) providing a sample containing HIV specific antibodies; b) performing an HIV infection confirmation assay on the sample; and c) performing an HIV infection recency determination assay on the sample; wherein step (b) and step (c) are performed simultaneously, thereby enabling simultaneous determination of HIV infection and HIV infection recency in the sample. In some embodiments, the method further comprises the step of: d) performing an HIV-1/HIV-2 infection differentiation assay on the sample; thereby enabling differentiation between HIV-1 and HIV-2 infection in the sample.

In other embodiments, the HIV infection confirmation assay is an immunoassay comprising a plurality of solid phases coated with antigens specific for HIV antibodies. In further embodiments, each of the plurality of solid phases is coated with a distinct HIV antigen derived from an HIV gag gene, an HIV env gene, or an HIV pol gene. In additional embodiments, the distinct HIV antigen derived from the HIV gag gene is capsid protein p24 or a fragment, variant, or derivative thereof. In further embodiments, the distinct HIV antigen derived from the HIV env gene is envelope protein gp160, gp120 or gp41 or a fragment, variant, or derivative thereof. In additional embodiments, the distinct HIV antigen derived from the HIV pol gene is regulatory protein p65 or a fragment, variant, or derivative thereof. In further embodiments, the sample is confirmed as an HIV positive sample when HIV specific antibodies against at least two HIV gene products are detected by the HIV infection confirmation assay.

In other embodiments, the HIV infection recency determination assay is an immunoassay comprising a solid phase undercoated with an HIV antigen. In further embodiments, an additional solid phase coated with an optimal amount of the same HIV antigen as the undercoat is used. In additional embodiments, the recency determination assay comprises detecting a signal from the solid phase and using the signal to determine whether the sample is from a recently HIV infected individual. In further embodiments, the sample is from a recently HIV infected individual when the signal is below a cutoff value.

In other embodiments, the HIV-1/HIV2 infection differentiation assay is an immunoassay comprising a solid phase coated with an antigen derived from an HIV-2 gene or a fragment, variant, or derivative thereof. In further embodiments, the immunoassay further comprises a second solid phase coated with a second antigen derived from an HIV-2 gene or a fragment, variant, or derivative thereof. In additional embodiments, the HIV-2 specific antigen is the GANN-5 peptide or a fragment, variant, or derivative thereof. In further embodiments, the sample is confirmed as an HIV-2 positive sample when HIV-2 specific antigens or fragments, variants, or derivatives thereof coating the solid phase are reactive with two or more antibodies in the sample.

In other embodiments, the solid phases within the HIV infection confirmation assay, HIV infection recency determination assay, and the HIV-1/HIV-2 infection differentiation assay are made of the same materials and are in separate reaction vessels. In additional embodiments, the reaction vessels are organized as a strip of vessels suitable for performing detection of antibodies in the sample. In further embodiments, the strip of vessels is a strip of a microwell plates comprising a plurality of wells. In additional embodiments, the reaction vessels are separate channels in a microfluidic device. In further embodiments, the reaction vessels are different spots on a piece of filter paper suitable for a lateral-flow or flow-through based assay. In additional embodiments, the reaction vessels are different microparticles coded with distinct markers.

In other embodiments, the HIV infection confirmation assay, HIV infection recency determination assay, and the HIV-1/HIV-2 infection differentiation assay are each enzyme-linked immunosorbent assays (ELISAs) or enzyme immunoassays (EIAs). In other embodiments, the assays comprise an HIV infection diagnostic or screening assay when the sample has not been previously tested with an HIV diagnostic or screening test.

In other embodiments, a method for estimating HIV incidence in a population is provided, the method comprising: a) providing a set of samples comprising HIV specific antibodies, wherein the set of samples is derived from a plurality of individuals within the population over a period of time; b) performing HIV infection recency determination assays on the set of samples; c) determining the percentage of recent HIV infections over the period of time; wherein the percentage of recent HIV infections over the period of time provides an estimate of HIV incidence in the population. In further embodiments, the period of time is 6 months, 12 months, 18 months, or 24 months. In additional embodiments, the HIV infection recency determination assay is an immunoassay comprising a solid phase undercoated with an HIV antigen. In further embodiments, an additional solid phase coated with an optimal amount of the same HIV antigen as the undercoat is used. In additional embodiments, the assays comprise detecting a signal from the solid phase and using the signal to determine whether a sample within the set of samples is from a recently HIV infected individual. In additional embodiments, the sample is from a recently HIV infected individual when the signal is below a cutoff value.

BRIEF DESCRIPTION OF THE FIGURES

Figure 1:
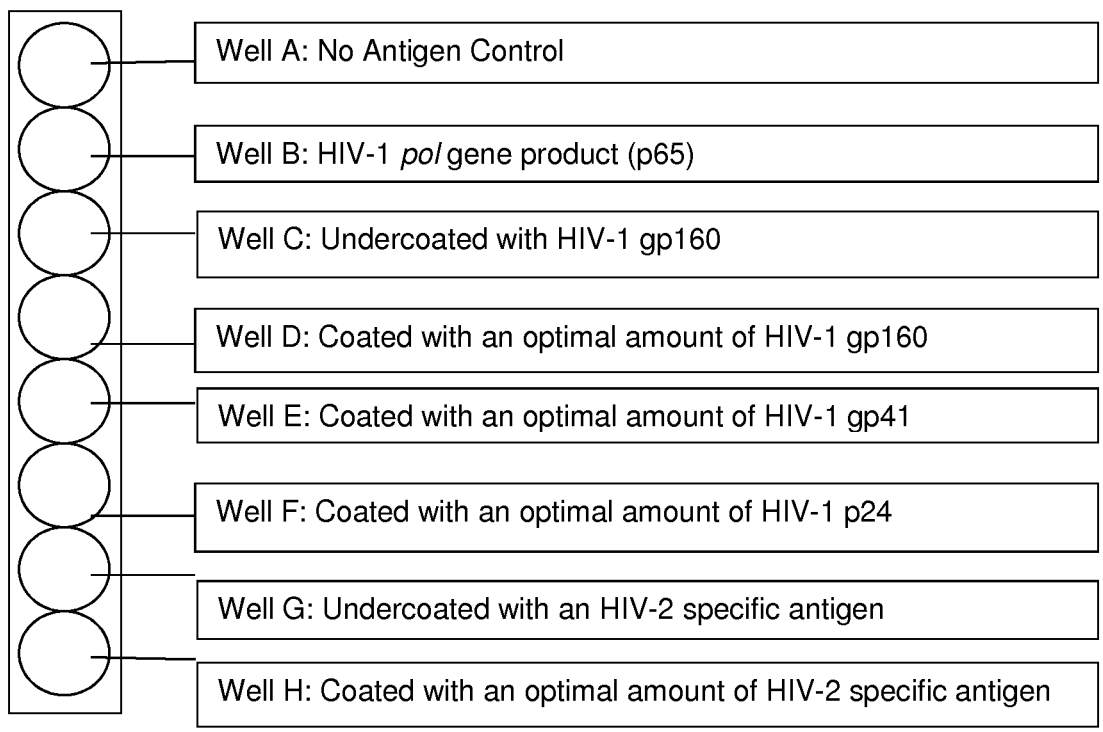

Having thus described the present invention in general terms, reference will now be made to the accompanying Drawings, which are not necessarily drawn to scale, and wherein:

FIG. 1 shows a diagram of an 8-well microwell strip coated with HIV-1 and HIV-2 antigens for use in confirmation and determination of recency of an HIV infection as well as for differentiation between HIV-1 and HIV-2 infection. Shown in the diagrams are first antigens (Wells D, E, F and H), second antigens (Wells C and G), third antigen (Well B) as well as a control well without coated HIV antigens (Well A). This design was used in Examples 2 and 3.

Figure 2:
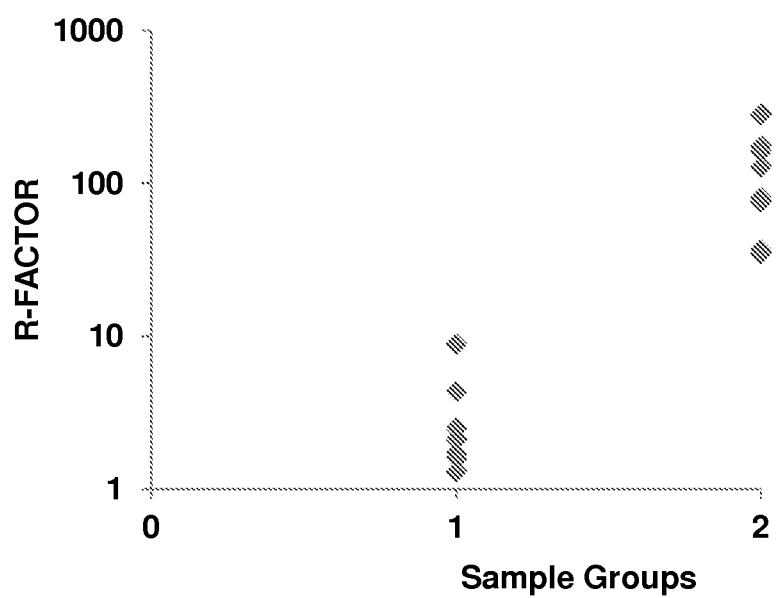

FIG. 2 shows a Recency Factor (R-Factor) Plot of samples from HIV-1 Recency/Prevalence Performance Panel PRB-601 from SeraCare. The R-Factor values are separated into two groups: all recency samples belong to the low R-Factor Group 1 while all prevalence samples belong to the high R-FACTOR factor Group 2.

Figure 3:
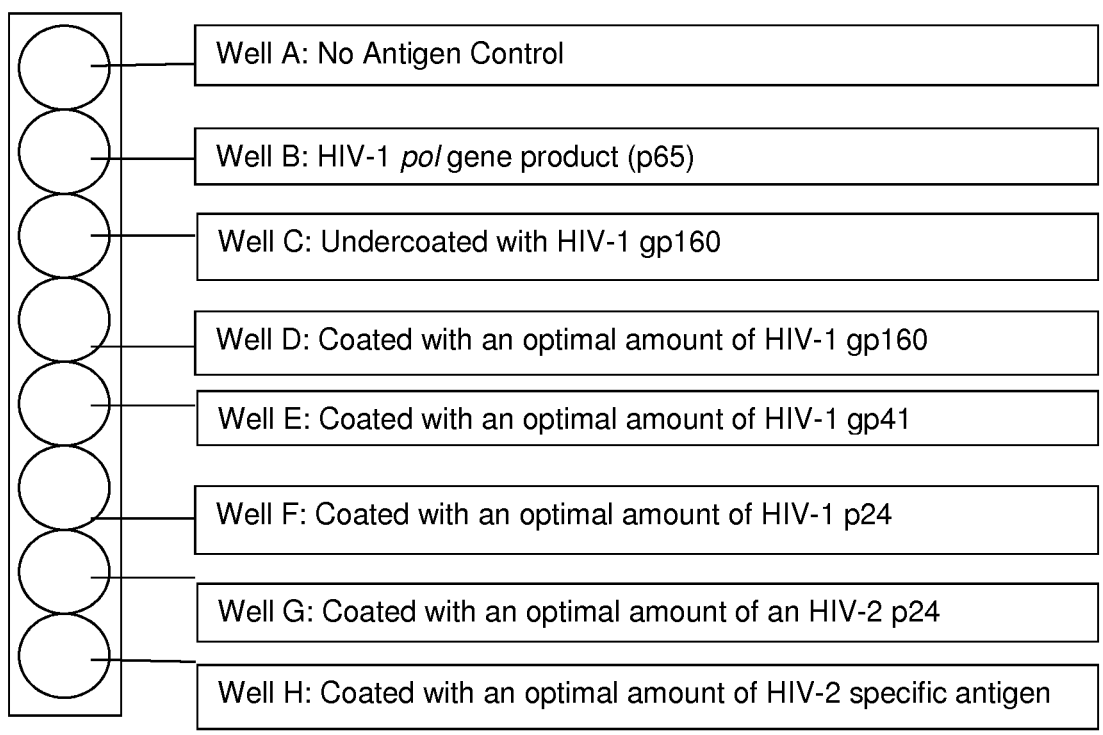

FIG. 3 shows a diagram of a variation of an 8-well microwell strip coated with HIV-1 and HIV-2 antigens for use in confirmation and determination of recency of an HIV infection as well as for differentiation between HIV-1 and HIV-2 infection. Shown in the diagrams are first antigens (Wells D, E, F and H), second antigens (Wells C and G), third antigen (Well B) as well as a control well without coated HIV antigens (Well A). This design is described in more detailed in Example 4.

DESCRIPTION OF THE INVENTION

The present invention will now be described more fully hereinafter with reference to the accompanying Figures, in which some, but not all embodiments of the inventions are shown. Like numbers refer to like elements throughout. The present invention may be embodied in many different forms and should not be construed as limited to the embodiments set forth herein; rather, these embodiments are provided so that this disclosure will satisfy applicable legal requirements. Indeed, many modifications and other embodiments of the present invention set forth herein will come to mind to one skilled in the art to which the present invention pertains having the benefit of the teachings presented in the foregoing descriptions and the associated Drawings. Therefore, it is to be understood that the present invention is not to be limited to the specific embodiments disclosed and that modifications and other embodiments are intended to be included within the scope of the appended claims.

The present invention provides a method which incorporates HIV infection recency testing into confirmatory testing, identification of HIV-1 from HIV-2 infections and/or diagnosis/screening testing of an HIV infection. The recency data may be used to estimate HIV incidence, i.e., the percentage of recent HIV infections in a given period of time, for example 1 year, in a given population. HIV incidence is an important tool for epidemiologic characterization, assessing the effectiveness of HIV/AIDS prevention program, and in the design and evaluation of HIV intervention trials.

In many countries, it is mandatory to perform a confirmatory testing for an HIV infection on a sample that is initially tested reactive with a diagnostic or screening test. An embodiment of the present invention is to incorporate a recency testing module into an HIV confirmatory testing module so that a recency test result is automatically and simultaneously generated when a sample is confirmed HIV positive with the test according to this invention. In another embodiment, an additional module for differentiation between HIV-1 and HIV-2 infection is incorporated into the test such that the test will confirm an HIV infection, tell whether the infection is a recent infection and determine whether it is an HIV-1 and/or HIV-2 infection. In still another embodiment, the test is used to screen samples with unknown HIV infection status for HIV infection.

The HIV confirmation and recency testing modules are immunoassays, which are organized in a manner that allows both modules to be performed simultaneously as a single assay. The immunoassays normally use HIV antigens coated onto solid phases for detection of HIV antibodies in a sample. Examples of appropriate solid phases include, but are not limited to, microwell plate wells, microwell plate strips, and other multiplex enabling solid phases. The HIV infection confirmation module consists of two or more solid phases, each of which is coated with an HIV antigen derived from a distinct HIV gene. An HIV infection is confirmed if antibodies against two or more individual HIV antigens derived from different HIV genes are detected. The recency testing module can be any serological tests so long as it is compatible with the HIV infection confirmation module, i.e., it can be performed along with the confirmation testing. An example of a recency testing module is a solid phase undercoated with an HIV antigen, i.e., coated with less than an optimal amount of HIV antigen such as HIV-1 gp160.

Since the antibody titers against and avidity for HIV antigens increase over time after an infection, an avidity and/or antibody titer measurement assay may be used for recency detection of an HIV infection. For example, the signal intensity from the solid phase with undercoated antigen had been showed to inversely correlate well with the recency of an HIV infection. The assay using an undercoated solid phase for recency detection was known as limiting antigen avidity EIA or LAg Avidity-EIA as shown in scientific publications (Wei et al., *Aids Res Hum Retroviruses*. 2010; 26:61 and Duong et al., *PLoS One*. 2012; 7:e33328), which are cited here solely as references. In certain embodiments, a solid phase with undercoated HIV antigen is incorporated into the HIV confirmation determination for detection of recency in HIV infection.

In another embodiment, an antigen is coated in two solid phases, one of which is optimally coated while the other is undercoated; the signals from both solid phases are used together for determination of recency of HIV infection. For example, the multiple of signals for the optimally coated and undercoated solid phases is used to indicate the recency of an infection. It is understood that the HIV antigen used for recency detection is reactive to a broad spectrum of HIV-1 strains or clades such that the strain difference does not cause significant difference in signal strength of the undercoated solid phase. A composite HIV-1 antigen composing of the immunedominant domain for all major HIV-1 Group M Clades may be used for detection of recency as described in a scientific publication (Wei et al., *Aids Res Hum Retroviruses* 2010; 26:61-71). It is also understood that conditions for optimally coating and/or undercoating the solid phase and cutoff value for recency detection need to be experimentally determined. Since infection of HIV-1 is the dominant type of HIV across the world, detection of recency may be focused on HIV-1 infections.

In other embodiment, a module for differentiation between HIV-1 and HIV-2 infection is incorporated into the test. Although HIV-2 infection is restricted to certain areas in the world, incorporation of an HIV-2 differentiation module will promote the use and adoption of the HIV infection confirmation and recency testing described in the present invention. An additional solid phase coated with an HIV-2 specific antibody may be used. An example of such an antigen is the GANN-5 antigen, which is specific for HIV-2 infection. Presence of antibodies to the HIV-2 specific antigen indicates an HIV-2 infection or HIV-1/HIV-2 coinfection.

Serologic assays are also commonly used for diagnosing/screening HIV infections using samples with unknown HIV infection status. The confirmation module may also be used for screening an HIV infection using a sample, which has not been tested with a serological diagnostic/screening test. Thus, in certain embodiments, the assay described in the present invention can be used for simultaneous diagnosis/screening for an HIV infection, confirmation of an infection, differentiation between HIV-1 and HIV-2 infection and determination of HIV infection recency.

The present invention is better understood by referring to Table 1, which lists the proteins encoded by the HIV genome. There are three classes of HIV proteins, the viral structural proteins, essential regulatory proteins/elements and accessory regulatory proteins. The three viral structural proteins, envelope protein gp120 and gp41 (or the uncleaved envelope protein gp160), capsid protein (CA or p24), and reverse transcriptase (p65), are commonly used for detection of HIV antibodies in a sample. An immunoassay normally contains a combination of these proteins, which are coated as a cocktail to a solid phase for detection of antibodies against these antigens. When a sample is reactive with the antigens in an immunoassay, the sample is further tested using a confirmatory assay such as the Western Blot assay, which can differentiate which HIV antigens are reactive with the antibodies in the sample. When the assay detects the presence of antibodies in the sample for at least two gene products, e.g., gp160 and p24, the individual from whom the sample is obtained is confirmed with HIV infection.

TABLE 1

Proteins Encoded by the HIV Genome

| Class | Gene name | Primary protein products | Processed protein products |
| --- | --- | --- | --- |
| Viral structural proteins | gag | Gag polyprotein | MA, CA (p24), SP1, NC, SP2, P6 |
|  | pol | Pol polyprotein | RT, RNase H, IN, PR |
|  | env | gp160 | gp120, gp41 |
| Essential regulatory elements | tat | Tat |  |
|  | rev | Rev |  |
| Accessory regulatory proteins | nef | Nef |  |
|  | vpr | Vpr |  |
|  | vif | Vif |  |
|  | vpu | Vpu |  |

In order to detect and differentiate antibodies against different antigens, different antigens are coated onto distinguishable solid phases. Appropriate solid phases include, but are not limited to, microwell plate wells, color coded microparticles, and microarrays, where a microwell, a microparticle coded with a particular color or a particular dot or position in a microarray is coated with a particular HIV antigen. Different HIV antigens are distinguished by the position of a microwell in a strip, the color of a microparticle, or the position in a microarray. Antibody specific for the antigen can be captured onto the solid phase and subsequently detected. In one embodiment, different antigens are coated onto a strip of microwells. At least two first antigens, e.g., gp160 and p24, are individually coated onto two separate microwells at optimal concentrations and then one or both are coated onto two different wells at reduced concentrations; the first antigens coated onto solid phases at reduced concentrations are referred to as the second antigens. Optionally, the pol gene product(s) may be coated as a third antigen onto another well at an optimal concentration. The well coated with the first antigens are used to confirm an infection of HIV while the second antigens, when used alone or in association with the signal from the first antigens, are used for determination of HIV recency. The third antigen can be used to provide additional information for determination of HIV recency.

A number of methods can be employed to detect the presence of antibodies specific for an HIV antigen. In a classic sandwich format, the human antibody bound to the solid phase via the coated HIV antigen is detected with a secondary antibody, i.e., goat anti-human IgG antibodies, which are conjugated with an enzyme such as horse radish hydrogen peroxidase (HRP). After washing, the enzyme bound to the solid surface is then detected using a substrate. In other embodiment, the enzyme is directly coupled to the same antigen as the one coated onto the solid phase. Since there are two binding sites in an antibody, the presence of an antibody specific for an HIV antigen can therefore be detected with an antigen conjugated with a detectable enzyme such as an HRP.

Variations can be made to the aforementioned assay. In some embodiments, a negative control, a solid phase coated with an HIV-2 specific antigen and/or HIV-1 group O antigen may be added to the assay. The negative control may be a solid phase without any coated HIV antigen. The HIV-2 specific antigen may be an HIV-2 specific peptide such as the GANN-5 peptide conjugated to bovine serum albumin (BSA). So is the HIV-1 group O specific antigen, which can also be a peptide conjugated to BSA.

In other embodiments, the solid phases are color-coded microparticles. Different HIV antigens are coated onto the microparticles coded with different colors. Color coding of microparticles may be accomplished by embedding the microparticles with fluorescent molecules with different colors. An HIV antigen is coated onto microparticles coded with one color. Bound antibodies specific for an HIV antigen can be detected with a secondary antibody labeled with a distinct fluorescent molecule or with the same antigen labeled with the fluorescent molecule. The microparticles can be separated and detected using a flow cytometer. In another embodiment, the solid phases are the dots in a microarray or similar platforms. The first, second and optionally third antigens are deposited onto different dots in a microarray. Bound antibodies may be detected with a secondary antibody or the antigen coupled with a detectable enzyme or chemical such as a fluorescent molecule.

As used herein, a "protein fragment" is a segment, domain, portion or region of a protein, which constitutes less than 100% of the amino acid sequence of the protein. For example, protein fragments may comprise up to 99%, 95%, 90%, 85%, 80%, 75%, 70%, 65%, 60%, 55%, 50%, 45%, 40%, 35%, 30%, 25%, 20%, 15%, 10%, 5%, 3%, 2% or 1% of said protein. In particular aspects, a protein fragment may comprise, for example, at least 5, 10, 20, 30, 40, 50 60, 70, 80, 90, 100, 120, 140, 150, 200, 250, 300, 350, 400, 450 or 500 contiguous amino acids of an HIV antigen. A peptide may be a protein fragment, for example comprising at least 6, 10, 12, 15, 20, 30, 40 and up to 50 contiguous amino acids.

As used herein. "variants" include within their scope naturally-occurring variants such as allelic variants, orthologs and homo logs and artificially created mutants, for example. The terms "mutant", "mutation" and "mutated" are used herein generally to encompass conservative or non-conservative amino acid substitutions, deletions and/or insertions introduced into an isolated protein or fragment thereof. Generally, protein variants have at least 80% amino acid sequence identity to an isolated protein of interest. In certain aspects of the present invention, protein variants have at least 85%, 90%, 91%, 92%, 93%, 94%, 95%, 96%, 97%, 98% or 99% amino acid sequence identity to an isolated protein of interest. Terms used to describe sequence relationships between respective nucleic acids or proteins include "comparison window", "sequence identity", "percentage of sequence identity" and "substantial identity." Because respective nucleotide or amino acid sequences may each comprise: (1) only one or more portions of a complete sequence that are shared by respective nucleic acids or proteins, and (2) one or more portions which are divergent between the nucleic acids or proteins, sequence comparisons are typically performed by comparing sequences over a "comparison window" to identify and compare local regions of sequence similarity. A "comparison window" refers to a conceptual segment of typically at least 6, 10, 12, 20 or more contiguous residues that is compared to a reference sequence. The comparison window may comprise additions or deletions (i.e., gaps) of about 20% or less (e.g. 5, 10 or 15%) as compared to the reference sequence (which does not comprise additions or deletions) for optimal alignment of the respective sequences. Optimal alignment of sequences for aligning a comparison window maybe conducted by computerized implementations of algorithms (for example ECLUSTALW and BESTFIT provided by WebAngis GCG, 2D Angis, GCG and GeneDoc programs, incorporated herein by reference) or by inspection and the best alignment (i.e., resulting in the highest percentage homology over the comparison window) generated by any of the various methods selected.

As used herein, a "derivative protein" is a protein which comprises one or more chemical and/or structural modifications or alterations of an amino acid sequence of interest. By way of example only, derivative proteins may comprise one or more modifications inclusive of amino acid side chain modifications, non-natural amino acids, glycosylated amino acid residues, cross-linked amino acid residues and/or additional amino acid residues. Derivatives also include within their scope isolated fusion proteins comprising additional amino acid sequences such as N- or C-terminal fusion partner sequences.

Isolated proteins of interest such as HIV antigens, inclusive of fragments, variants and derivatives, may be made in recombinant or chemical synthetic form. Generally, recombinant proteins may be conveniently prepared by a person skilled in the art using standard protocols commonly known in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

A Stripwell Assay for Confirmation of HIV Infection and Determination of Recency of an HIV Infection This example uses a standard microwell plate, which contains 12 strips. Each strip contains 8 wells. The microwells are used as the solid phase for coating HIV antigens. As illustrated in FIG. 1, the eight microwells in a strip are coated with HIV-1 and HIV-2 antigens for use in confirmation of an HIV-1 or HIV-2 infection and determination of recency of the HIV infection.

The first antigens for HIV-1 are gp160, gp41, and p24, which are coated in Wells D, E and F while the first antigens for HIV-2 is the GANN-5 peptide coupled to BSA, which is coated onto Well H. The second antigens for HIV-1 and HIV-2 are gp160 and the GANN-5 peptide coupled to BSA, which are coated in Wells C and G, respectively, at reduced concentration as compared to the corresponding first antigens. The third antigen is the pol gene product (herein referred to as p65), which is coated on Well B at an optimal concentration. In addition, there is a negative control well (Well A), which contains no coated HIV antigens.

Since a sample from an individual recently infected with HIV is expected to contain a lower antibody titer and less avidity antibodies, little or no signal is expected in wells coated with the second antigens while the antibody can still be detected at a significant signal level in wells coated with the first antigens.

Example 2

An Assay for Diagnosing and/or Confirming an HIV Infection

Recombinant proteins substantially equivalent to HIV-1 gp160, gp41, p24 and full length pol gene product were produced in a mammalian cell line (for gp160) or in *E. coli* (for gp41, p24 and the poi gene product). The HIV-2 GANN-5 peptide was synthesized and coupled to BSA using well established chemistry. Optimal concentrations of HIV-1 gp160, gp41, p24, pol gene product (p65) and HIV-2 GANN-5 peptide coupled to BSA were coated onto Wells D, E, F, B and H, respectively. Reduced concentrations of HIV-1 gp160 and HIV-2 GANN-5 peptide coupled to BSA were coated to Wells C and G, respectively. No antigen was coated to Well A, which was used as a negative control.

To detect the antibodies specific for gp160, gp41, p65, and HIV-2 GNN-5, these HIV antigens (gp160, p65 and HIV-2 GANN-5) were conjugated to horse radish peroxidase (HRP). For detection of p24, biotinylated p24 and avidin-HRP conjugate were used.

To perform detection, the antigen coated microwell strips were first soaked with 80 microliters of sample diluent buffer such as PBS followed by addition of 20 microliters of sample to each well. After incubation, the samples were removed and then washed four times with a wash buffer. The wells were then incubated with a solution containing biotinylated p24. After washing, the wells were loaded with a solution containing HRP conjugated to gp160, p65, HIV-2 GANN-5 and avidin. Following incubation, the solutions in the wells were removed and the wells were washed four times. The captured HRP was detected with a solution containing the HRP substrate 3,3',5,5'-Tetramethylbenzidine (TMB), which changes in color after reaction with HRP. It is understood that assay conditions such as incubation time and temperature need to be optimized for each assay.

A cutoff value may be determined by averaging the absorbance for all the wells in a strip, which was incubated with a negative control sample. A signal above the cutoff value (i.e., signal to cutoff value, S/CO, greater than 1.0) is considered positive. If the S/CO values for two or more of the first HIV-1 antigen wells are above 1.0, then the individual who donated the sample is confirmed positive for HIV-1 infection.

An assay was prepared essentially as described above and used for detection of human samples. Ten negative human serum and ten negative plasma samples were tested according to the protocol described above. Signal to cutoff values were calculated and are presented in Table 2 (serum samples) and Table 3 (plasma sample). As expected, all samples had S/CO less than 1.0 for all wells, indicating that the assay did not react non-specifically.

TABLE 2

Random Serum Samples from a Low Risk Population (S/CO Values)

| Well # | Coated Antigen | Human Serum Sample Number | | | | | | | | | |
|---|---|---|---|---|---|---|---|---|---|---|---|
| | | 1 | 2 | 3 | 4 | 5 | 6 | 7 | 8 | 9 | 10 |
| A | No Antigen | 0.429 | 0.404 | 0.413 | 0.413 | 0.413 | 0.413 | 0.413 | 0.438 | 0.455 | 0.438 |
| B | HIV-1 p65 | 0.472 | 0.480 | 0.505 | 0.480 | 0.851 | 0.497 | 0.589 | 0.463 | 0.522 | 0.480 |
| C | HIV-1 gp160 (reduced level) | 0.404 | 0.396 | 0.404 | 0.396 | 0.413 | 0.404 | 0.421 | 0.396 | 0.421 | 0.404 |
| D | HIV-1 gp160 | 0.463 | 0.480 | 0.514 | 0.472 | 0.480 | 0.488 | 0.480 | 0.480 | 0.480 | 0.472 |
| E | HIV-1 gp41 | 0.413 | 0.429 | 0.421 | 0.429 | 0.446 | 0.421 | 0.455 | 0.421 | 0.404 | 0.446 |
| F | HIV-1 p24 | 0.404 | 0.404 | 0.446 | 0.413 | 0.421 | 0.396 | 0.472 | 0.396 | 0.379 | 0.396 |
| G | HIV-2 peptide (reduced level) | 0.404 | 0.404 | 0.413 | 0.429 | 0.429 | 0.438 | 0.531 | 0.396 | 0.396 | 0.429 |
| H | HIV-2 Peptide | 0.421 | 0.421 | 0.421 | 0.472 | 0.413 | 0.421 | 0.421 | 0.446 | 0.497 | 0.404 |

TABLE 3

Random Plasma Samples from a Low Risk Population (S/CO Values)

| Well # | Coated Antigen | Human Plasma Sample Number | | | | | | | | | |
|---|---|---|---|---|---|---|---|---|---|---|---|
| | | 1 | 2 | 3 | 4 | 5 | 6 | 7 | 8 | 9 | 10 |
| A | No Antigen | 0.389 | 0.439 | 0.422 | 0.398 | 0.389 | 0.381 | 0.422 | 0.414 | 0.464 | 0.422 |
| B | HIV-1 p65 | 0.472 | 0.472 | 0.563 | 0.505 | 0.480 | 0.530 | 0.555 | 0.513 | 0.505 | 0.522 |
| C | HIV-1 gp160 (reduced level) | 0.373 | 0.389 | 0.398 | 0.373 | 0.381 | 0.389 | 0.398 | 0.381 | 0.389 | 0.422 |
| D | HIV-1 gp160 | 0.472 | 0.464 | 0.464 | 0.464 | 0.513 | 0.455 | 0.472 | 0.489 | 0.522 | 0.497 |
| E | HIV-1 gp41 | 0.455 | 0.422 | 0.398 | 0.406 | 0.431 | 0.398 | 0.398 | 0.389 | 0.414 | 0.414 |
| F | HIV-1 p24 | 0.381 | 0.373 | 0.381 | 0.389 | 0.389 | 0.373 | 0.381 | 0.373 | 0.373 | 0.381 |
| G | HIV-2 peptide (reduced level) | 0.389 | 0.389 | 0.389 | 0.389 | 0.389 | 0.381 | 0.480 | 0.381 | 0.381 | 0.439 |
| H | HIV-2 Peptide | 0.406 | 0.406 | 0.398 | 0.439 | 0.389 | 0.389 | 0.398 | 0.389 | 0.414 | 0.389 |

Test results of six wells (Wells A, B, D, E, F and H) were used for detection of HIV antibodies in the samples as a means for diagnosing and/or confirming an HIV infection. Signal (Signal to cutoff) of Well A served as a negative test control and was expected to be less than 1.0 in order for the assay to be valid. Wells B, D, E and F were used for detection of HIV-1 and/or HIV-2 infection whereas Well H was used for differentiation between HIV-1 and HIV-2 infection (see Example 3 for differentiation between HIV-1 and HIV-2 infections). To confirm an HIV infection, the sample should contain antibodies reactive to at least two HIV antigens derived from different HIV gene.

Ten HIV-1 positive human samples were tested using the assay. The S/CO values of these ten HIV-1 positive samples showed four HIV-1 antibody reactivity patterns (Table 4). Samples 1, 3, and 8 contain antibodies to HIV-1 major gene products pol (p65), env (gp160, gp41), and gag (p24). The antibody level to gp160 appeared to be high as indicated by reactive results (>2.0 S/CO) even in wells coated with a reduced concentration of gp160 (Well C). Samples 2, 6, 7, and 10 contain antibodies to the same HIV-1 major gene products but the antibody level to gp160 appeared to be low as indicated by nonreactive results in wells coated with a reduced concentration of gp160 (Well C). These samples might have been from individuals with recent HIV-1 infection.

Samples 4 and 5 contained antibodies to the same HIV-1 major gene products but the antibody level to gp160 appeared to be intermediate as indicated by low reactive (S/CO 1.0-2.0) in wells coated with a reduced concentration of gp160 (Well C).

Sample 9 contained antibodies to HIV-1 env (gp160, gp41) and gag (p24) only, with no reactivity to pol (p65). The antibody level to gp160 appeared to be low as indicated by nonreactive result in wells coated with a reduced concentration of gp160 (Well C).

Since each of these 10 HIV-1 samples contained antibodies reactive to at least two antigens derived from at least two HIV-1 genes and not to the HIV-2 specific antigen (Table 3), all these samples were diagnosed and confirmed HIV-1 infection.

TABLE 4

Detection of HIV-1 Antibody Positive Samples (S/CO Values)

| Well # | Coated Antigen | Sample Number | | | | | | | | | |
|---|---|---|---|---|---|---|---|---|---|---|---|
| | | 1 | 2 | 3 | 4 | 5 | 6 | 7 | 8 | 9 | 10 |
| A | No Antigen | 0.413 | 0.440 | 0.422 | 0.457 | 0.431 | 0.431 | 0.431 | 0.527 | 0.475 | 0.431 |
| B | HIV-1 p65 | 31.103 | 5.547 | 15.930 | 15.385 | 15.138 | 15.288 | 1.275 | 28.809 | 0.993 | 15.938 |
| C | HIV-1 gp160 | 5.292 | 0.510 | 2.215 | 1.081 | 1.020 | 0.923 | 0.422 | 5.864 | 0.422 | 0.545 |

TABLE 4-continued

Detection of HIV-1 Antibody Positive Samples (S/CO Values)

| Well # | Coated Antigen | Sample Number | | | | | | | | | |
|---|---|---|---|---|---|---|---|---|---|---|---|
| | | 1 | 2 | 3 | 4 | 5 | 6 | 7 | 8 | 9 | 10 |
| D | HIV-1 gp160 (reduced level) | 32.800 | 12.738 | 32.105 | 22.101 | 26.884 | 20.967 | 2.804 | 34.251 | 4.589 | 13.345 |
| E | HIV-1 gp41 | 28.519 | 10.145 | 30.910 | 16.730 | 19.657 | 11.429 | 1.829 | 31.886 | 2.857 | 9.574 |
| F | HIV-1 p24 | 1.415 | 31.059 | 20.897 | 34.356 | 11.138 | 33.415 | 11.024 | 34.145 | 29.829 | 33.679 |
| G | HIV-2 peptide (reduced level) | 0.431 | 0.457 | 0.422 | 0.448 | 0.484 | 0.422 | 0.431 | 0.782 | 0.413 | 0.422 |
| H | HIV-2 Peptide | 0.466 | 0.440 | 0.492 | 0.440 | 0.440 | 0.448 | 0.448 | 0.615 | 0.413 | 0.413 |

HIV-1 is classified into several genetically distinct Clades (subtypes). Table 5 shows the S/CO values from eight samples representing various HIV-1 group M clades. Due to limited volumes of the samples, all were diluted 1:100 prior to testing. Despite the dilution, Clades A to G were reactive to three HIV-1 gene products; pol (p65), env (gp160, gp41), and gag (p24). Clade H was reactive to two HIV-1 gene products; pol (p65) and env (gp160, gp41). None of them showed reactivity to the HIV-2 peptide antigen (Wells G and H). Thus, these samples were confirmed with HIV-1 infection.

TABLE 5

HIV-1 Clade Samples (S/CO Values)

| Well # | Coated Antigen | HIV-1 Clade | | | | | | | |
|---|---|---|---|---|---|---|---|---|---|
| | | A | B | C | D | E | F | G | H |
| A | No Antigen | 0.391 | 0.383 | 0.399 | 0.391 | 0.399 | 0.407 | 0.391 | 0.431 |
| B | HIV-1 p65 | 9.533 | 26.874 | 13.741 | 16.703 | 9.868 | 19.337 | 11.178 | 3.114 |
| C | HIV-1 gp160 (reduced level) | 4.423 | 2.443 | 1.764 | 0.447 | 2.403 | 0.695 | 3.984 | 1.733 |
| D | HIV-1 gp160 | 29.517 | 29.317 | 28.152 | 8.703 | 30.275 | 16.216 | 30.124 | 24.016 |
| E | HIV-1 gp41 | 19.010 | 18.092 | 18.451 | 6.435 | 16.152 | 9.876 | 13.126 | 8.639 |
| F | HIV-1 p24 | 31.305 | 26.244 | 31.074 | 30.707 | 30.675 | 31.737 | 30.882 | 0.463 |
| G | HIV-2 peptide (reduced level) | 0.407 | 0.407 | 0.399 | 0.471 | 0.455 | 0.415 | 0.399 | 0.391 |
| H | HIV-2 Peptide | 0.407 | 0.399 | 0.407 | 0.415 | 0.447 | 0.439 | 0.399 | 0.423 |

Example 3

Use of the Assay for Differentiation Between HIV-1 and HIV-2 Infections

Wells G and H in the assay described in Examples 1 and 2 were coated with an HIV-2 specific peptide antigen, GANN-5 although Well G was undercoated. A sample containing antibodies reactive to this antigen in Well H indicates an HIV-2 infection. Table 6 shows S/CO values of ten HIV-2 antibody positive samples. All ten samples exhibited antibody reactivity to the HIV-2 specific peptide.

TABLE 6

Detection of HIV-2 Antibody Positive Samples (S/CO Values)

| Well # | Coated Antigen | Sample Number | | | | | | | | | |
|---|---|---|---|---|---|---|---|---|---|---|---|
| | | 1 | 2 | 3 | 4 | 5 | 6 | 7 | 8 | 9 | 10 |
| A | No Antigen | 0.411 | 0.428 | 0.411 | 0.463 | 0.411 | 0.428 | 0.454 | 0.331 | 0.358 | 0.364 |
| B | HIV-1 p65 | 0.522 | 1.054 | 0.600 | 1.019 | 17.345 | 15.520 | 0.582 | 1.133 | 0.616 | 2.120 |
| C | HIV-1 gp160 (reduced level) | 0.394 | 0.403 | 0.403 | 0.411 | 0.403 | 0.420 | 0.428 | 0.331 | 0.311 | 0.325 |
| D | HIV-1 gp160 | 0.471 | 0.557 | 0.548 | 0.591 | 0.822 | 0.668 | 0.480 | 0.550 | 0.411 | 0.563 |
| E | HIV-1 gp41 | 0.437 | 0.668 | 0.454 | 0.934 | 0.497 | 0.557 | 0.454 | 0.682 | 0.477 | 1.948 |
| F | HIV-1 p24 | 2.381 | 11.092 | 0.411 | 33.619 | 0.445 | 11.863 | 0.694 | 14.841 | 2.213 | 14.801 |
| G | HIV-2 peptide (reduced level) | 0.959 | 1.319 | 0.668 | 1.585 | 0.540 | 1.319 | 1.028 | 0.881 | 0.934 | 1.285 |
| H | HIV-2 Peptide | 28.171 | 32.231 | 17.867 | 32.206 | 8.985 | 30.835 | 29.370 | 22.851 | 22.831 | 24.368 |

Example 4

Use of the Assay for HIV-1 Infection Recency Determination

The assay described in Examples 1-3 contained two wells undercoated with an HIV antigen. Well C was undercoated with HIV-1 gp160 while Well G was undercoated with HIV-2 peptide antigen. The signal from the undercoated wells alone or along with the well optimally coated with the same antigen may be used for determination of HIV infection recency. Since there were few HIV-2 recency samples available, the assay's capability to determine infection recency was evaluated using relevant HIV-1 samples using the signal from HIV-1 gp160 coated wells.

Tables 7 and 8 show S/CO values of 15 plasma samples from HIV-1 Recency/Prevalence Performance Panel PRB-601 from SeraCare (Milford, Mass.). Recency samples were obtained from individuals with new or short term HIV-1 infections. Prevalence (long-term infection) samples were obtained from individuals with chronic or long term HIV-1 infections. All samples in the panel contain antibodies to three HIV-1 gene products; pol (p65), env (gp160, gp41), and gag (p24).

As shown in Table 7, the recency samples, which were collected from individuals with recent infections, were non-reactive in wells coated with a reduced level of gp160 (Well C) with a S/CO of less than 1.0. In contrast, all of the prevalence samples, which were collected from individuals who had been known to be infected with HIV for a longer period of time, were either low reactive (Samples 6 and 15 with S/CO values between 1.0 and 2.0) or reactive (samples 3, 4, 8, 10, 11 and 13 with S/CO values >2.0) in wells coated with a reduced level of gp160 (Table 7). Thus, the signal from the well undercoated with HIV-1 gp160 alone was sufficient to determine recency of HIV-1 infection.

The signals from both optimally coated and undercoated HIV-1 gp160 (Wells C and D) may be used together to determine the infection recency as well. The signal multiple of Well C and D, which is denoted here as R-Factor, may be used to indicate the recency of infection. The R-Factor values for all recency samples were less than 9.0 with a mean of 3.21 ranging from 1.30 to 8.98 (Table 7). In contrast, the R-Factor values for all prevalence samples were more than 34.0 with a mean of 122.29 ranging from 34.95 to 284.03 (Table 8). Based on the R-Factor values, the recency and prevalence samples were clearly separated into two groups: low R-Factor value group for recency samples and high R-Factor value group for the prevalence samples (FIG. 2).

TABLE 7

Recency Samples from Panel PRB-601 (S/CO Values)

| Well # | Coated Antigen | 1 | 2 | 5 | 7 | 9 | 12 | 14 |
|---|---|---|---|---|---|---|---|---|
| A | No Antigen | 0.401 | 0.426 | 0.418 | 0.426 | 0.459 | 0.398 | 0.406 |
| B | HIV-1 p65 | 4.392 | 2.280 | 1.879 | 1.077 | 6.873 | 17.905 | 22.385 |
| C | HIV-1 gp160 (reduced level) | 0.434 | 0.418 | 0.401 | 0.434 | 0.468 | 0.571 | 0.398 |
| D | HIV-1 gp160 | 4.885 | 4.092 | 3.958 | 5.787 | 9.269 | 15.569 | 3.255 |
| E | HIV-1 gp41 | 3.883 | 3.023 | 6.280 | 3.691 | 8.234 | 11.313 | 2.692 |
| F | HIV-1 p24 | 29.954 | 30.213 | 12.952 | 14.555 | 20.585 | 32.041 | 10.559 |
| G | HIV-2 peptide (reduced level) | 0.409 | 0.401 | 0.443 | 0.401 | 0.409 | 0.422 | 0.422 |
| H | HIV-2 Peptide | 0.409 | 0.401 | 0.418 | 0.392 | 0.426 | 0.414 | 0.398 |
| | R-Factor | 2.12 | 1.71 | 1.59 | 2.51 | 4.34 | 8.89 | 1.30 |

TABLE 8

Prevalence (Long-Term) Samples from Panel PRB-601 (S/CO Values)

| Well # | Coated Antigen | 3 | 4 | 6 | 8 | 10 | 11 | 13 | 15 |
|---|---|---|---|---|---|---|---|---|---|
| A | No Antigen | 0.418 | 0.418 | 0.434 | 0.493 | 0.409 | 0.389 | 0.406 | 0.406 |
| B | HIV-1 p65 | 19.324 | 29.177 | 8.384 | 27.916 | 29.344 | 28.389 | 16.820 | 25.300 |
| C | HIV-1 gp160 (reduced level) | 2.614 | 4.058 | 1.370 | 8.860 | 5.628 | 5.226 | 2.534 | 1.342 |
| D | HIV-1 gp160 | 30.873 | 31.691 | 27.006 | 32.058 | 31.140 | 30.915 | 30.079 | 26.046 |
| E | HIV-1 gp41 | 24.117 | 24.326 | 22.514 | 32.401 | 30.455 | 29.193 | 29.913 | 16.472 |
| F | HIV-1 p24 | 31.775 | 32.209 | 27.641 | 32.084 | 6.205 | 28.447 | 32.141 | 32.240 |
| G | HIV-2 peptide (reduced level) | 0.451 | 0.434 | 0.468 | 0.618 | 0.409 | 0.422 | 0.431 | 0.464 |
| H | HIV-2 Peptide | 0.426 | 0.418 | 0.409 | 0.501 | 0.409 | 0.414 | 0.455 | 0.431 |
| | R-Factor | 80.70 | 128.60 | 37.00 | 284.03 | 175.26 | 161.56 | 76.22 | 34.95 |

The assay described in Examples 1-4 was further evaluated for HIV infection recency determination using a sample panel from CEPHIA (Consortium for the Evaluation and Performance of HIV Incidence Assays). These samples are considered well characterized HIV recency samples. In this sample panel, there were 25 HIV negative samples and 75 HIV-1 positive samples. Of the 75 HIV-1 positive samples, 25 were collected from individuals within 12 months of infection ($12^{th}$ month included) and 50 were from individuals beyond 12 months infection. These HIV negative and positive samples were tested using the assay described in Examples 1-4. All 25 HIV negative samples were nonreactive while all 75 HIV-1 positive samples were confirmed for HIV-1 positive with the assay.

The R-FACTOR values, i.e., the signal multiple from wells optimally coated and undercoated coated with HIV-1 gp160 was computed for each sample. As shown in Table 9, the R-Factor values increased over time after infection and correlated well with the recency of HIV infections. To further estimate the accuracy of the assay for determination of HIV infection recency, the HIV-1 positive samples were divided into groups: those that were collected in the first 12 months after HIV infection (recent infection) and those that were collected after 12 months post infection (prevalent/long-term infection). The accuracy of the assay was estimated by comparison of its test results with those of the expected results, which are considered here as the gold standard results. Using an R-Factor value of 20 as the cutoff, the assay according to the present invention had an 88% and 96% accuracy for detecting recent and prevalent/long-term samples, respectively (Table 10). The assay could accurately determine the recency of HIV infection. Thus, the assay according to the present invention could be used for simultaneous confirmation of HIV infections and determination of recency of HIV infections.

Example 5

Variations of the Assay

Many variations of the assay described in Examples 1-4 may be constructed by those skilled in the art to achieve the same main objective. Other variations may have additional or different accessory functions. In this example, the well coated with undercoated HIV-2 specific antigen is replaced with an optimally coated HIV-2 gag gene product (p24) as the antigen as depicted in FIG. 3. As the HIV-2 specific peptide (GANN-5) is derived from HIV-2 gp36, the assay in this example has two wells, each of which is optimally coated with an antigen derived from different HIV-2 genes, and can be used to confirm an HIV-2 infection.

Thus, the assay in this example can be used for confirmation of HIV-1 and/or HIV-2 infection, differentiation between HIV-1 and HIV-2 infection and determination of the recency of an HIV infection.

The results from these studies described in Examples 1-4 showed that the assays prepared according to the present invention can be used to simultaneously confirm an HIV infection, differentiate between HIV-1 and/or HIV-2 infection, and determine the recency of an HIV infection. It is understood that variations of the assays, one of which is described in Example 5, can be prepared by those skilled in the art to achieve the same main objective.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

TABLE 9

Testing on CEPHIA Panel Using the Assay According to the Invention

| Sample Type | | N | Mean R-FACTOR Factor |
|---|---|---|---|
| HIV Negative | | 25 | 0.30 |
| HIV-1 Positive | <6 Months | 21 | 11.43 |
| (Months after infection) | 6-12 Month | 4 | 21.78 |
| | 12-24 Month | 11 | 109.98 |
| | >24 Months | 39 | 113.16 |

TABLE 10

Assay Accuracy for HIV-1 Infection Recency Determination

| | | Cohort Study Based Estimation | |
|---|---|---|---|
| | | Recent (<12 month) | Prevalent (≥12 month) |
| Estimation based on the assay according to the present invention | Recent (R-FACTOR <20) | 22 | 2 |
| | Prevalent (IP ≥ 20) | 3 | 48 |
| | Sensitivity[1] | =22/25 = 88.00% | |
| | Specificity[2] | =48/50 = 96.00% | |

[1]Sensitivity of the assay is the percentage of the HIV-1 positive samples collected within 12 months ($12^{th}$ month included) determined to be recent infection samples by the assay according to the invention;
[2]Specificity of the assay is the percentage of the HIV-1 positive sample collected after an infection for more than 12 months determined to be prevalent samples by the assay according to the invention;

We claim:

1. A method for determination of HIV infection and estimation of HIV infection recency, the method comprising the steps of:
   a) providing a sample comprising HIV specific antibodies;
   b) performing an HIV infection confirmation assay on the sample;
   c) performing an HIV infection recency determination assay on the sample; and
   d) performing an HIV-1 / HIV-2 infection differentiation assay on the sample comprising the use of an HIV-2 specific antigen;
wherein step (b) through step (d) are performed simultaneously in a single assay, thereby enabling simultaneous determination of HIV infection, HIV infection recency, and HIV-1 / HIV-2 differentiation in the sample.

2. The method of claim 1, wherein the HIV infection confirmation assay is an immunoassay comprising a plurality of solid phases coated with antigens specific for HIV antibodies.

3. The method of claim 2, wherein each of the plurality of solid phases is coated with a distinct HIV antigen derived from an HIV gag gene, an HIV env gene, or an HIV pol gene.

4. The method of claim 3, wherein the distinct HIV antigen derived from the HIV gag gene is capsid protein p24 or a fragment, variant, or derivative thereof.

5. The method of claim 3, wherein the distinct HIV antigen derived from the HIV env gene is envelope protein gpl60, gpl20 or gp41 or a fragment, variant, or derivative thereof.

6. The method of claim 3, wherein the distinct HIV antigen derived from the HIV pol gene is regulatory protein p65 or a fragment, variant, or derivative thereof.

7. The method of claim 1, wherein step b) further comprises detection of HIV specific antibodies and wherein the sample is confirmed as an HIV positive sample when HIV specific antibodies against at least two HIV gene products are detected by the HIV infection confirmation assay.

8. The method of claim 1, wherein the HIV infection recency determination assay is an immunoassay comprising a first solid phase undercoated with an HIV antigen.

9. The method of claim 2, wherein the immunoassay for HIV infection recency determination assay comprises a second solid phase coated with an optimal amount of the same HIV antigen as the undercoat.

10. The method of claim 8, comprising detecting a signal from the first solid phase and using the signal to determine whether the sample is from a recently HIV infected individual.

11. The method of claim 9, comprising detecting a signal from said first and second solid phases and using a signal multiple (R-Factor) of the two solid phases to determine whether the sample is from a recently HIV infected individual.

12. The method of claim 10, wherein the sample is from a recently HIV infected individual when the signal is below a cutoff value.

13. The method of claim 1, wherein the HIV-1/HIV-2 infection differentiation assay is an immunoassay comprising a solid phase coated with the HIV-2 specific antigen.

14. The method of claim 1, wherein the HIV infection confirmation assay is an immunoassay comprising a plurality of solid phases coated with antigens specific for HIV antibodies and wherein the HIV infection recency determination assay is an immunoassay comprising a solid phase undercoated with an HIV antigen that is the same as one of the HIV antigens used for confirmation of an HIV infection.

15. The method of claim 13, wherein the immunoassay further comprises a second solid phase coated with a second HIV-2 specific antigen.

16. The method of claim 13, wherein the HIV-2 specific antigen is the GANN-5 peptide or a fragment, variant, or derivative thereof.

17. The method of claim 13 wherein the sample is confirmed as an HIV-2 positive sample when HIV-2 specific antigens or fragments, variants, or derivatives thereof coating the solid phase are reactive with one or more antibodies in the sample.

18. The method of claim 13, wherein the solid phases are made of the same materials and are in separate reaction vessels.

19. The method of claim 18, wherein the reaction vessels are organized as a strip of vessels suitable for performing detection of antibodies in the sample.

20. The method of claim 18, wherein the strip of vessels is a strip of microwell plates comprising a plurality of wells.

21. The method of claim 18, wherein the reaction vessels are separate channels in a microfluidic device.

22. The method of claim 18, wherein the reaction vessels are different spots on a piece of filter paper suitable for a lateral-flow or flow-through based assay.

23. The method of claim 17, wherein the reaction vessels are different microparticles coded with distinct markers.

24. The method of claim 18, wherein the reaction vessels are different dots on a solid phase.

25. The method of claim 24, wherein the different dots on a solid phase are in a microarray assay.

26. The method of claim 1, wherein the assays are enzyme-linked immunosorbent assays (ELISAs) or enzyme immunoassays (EIAs).

27. The method of claim 1, wherein the assays comprise an HIV infection diagnostic or screening assay when the sample has not been previously tested with an HIV diagnostic or screening test.

28. A method for estimating HIV incidence in a population, the method comprising:
   a) providing a set of samples comprising HIV specific antibodies, wherein the set of samples is derived from a plurality of individuals within the population over a period of time;
   b) performing HIV infection confirmation assays on the set of samples;
   c) performing HIV infection recency determination assays on the set of samples;
   d) determining the percentage of recent HIV infections over the period of time;
wherein the percentage of recent HIV infections over the period of time provides an estimate of HIV incidence in the population; and
   e) performing an HIV-1/HIV-2 infection differentiation assay on the sample comprising the use of an HIV-2 specific antigen;
wherein step (b) through step (e) are performed simultaneously in a single assay, thereby enabling simultaneous determination of HIV infection, HIV infection recency, and HIV-1/HIV-2 differentiation in the sample.

29. The method of claim 28, wherein the period of time is 6 months.

30. The method of claim 28, wherein the period of time is 12 months.

31. The method of claim 28, wherein the period of time is 18 months.

32. The method of claim 28, wherein the period of time is 24 months.

33. The method of claim 28, wherein the HIV infection recency determination assay is an immunoassay comprising a first solid phase undercoated with an HIV antigen.

34. The method of claim 33, wherein the HIV infection recency determination assay comprises a second solid phase coated with optimal amounts of the same HIV antigen as the undercoat.

35. The method of claim 28, comprising detecting a signal from the first and second solid phases and using a signal multiple (R-Factor) of the first and second solid phases to determine whether the sample is from a recently HIV infected individual.

36. The method of claim 33, comprising detecting a signal from the first solid phase and using the signal to determine whether the sample is from a recently HIV infected individual.

37. The method of claim 36, wherein the sample is from a recently HIV infected individual when the signal multiple is below a cutoff value.

38. The method of claim 35, wherein the sample is from a recently HIV infected individual when the signal multiple is below a cutoff value.

39. The method of claim 11, wherein the sample is from a recently HIV infected individual when the signal multiple is below a cutoff value.

40. The method of claim 15, wherein the HIV-2 specific antigen is the GANN-5 peptide or a fragment, variant, or derivative thereof.

* * * * *